United States Patent [19]

Copes

[11] 4,442,554
[45] Apr. 17, 1984

[54] BIOMECHANICAL ANKLE DEVICE

[76] Inventor: Arthur Copes, P.O. Box 42, French Settlement, La. 70733

[21] Appl. No.: 348,284

[22] Filed: Feb. 12, 1982

[51] Int. Cl.³ .............................................. A61F 11/04
[52] U.S. Cl. ........................................................ 3/35
[58] Field of Search ..................... 3/5, 6, 7, 30, 31, 32, 3/33, 34, 35

[56] References Cited

U.S. PATENT DOCUMENTS

| 2,368,917 | 2/1945 | Dumelin | 3/35 |
| 2,556,525 | 6/1951 | Drennon | 3/32 |
| 3,874,004 | 4/1975 | May | 3/7 X |

FOREIGN PATENT DOCUMENTS 325333  9/1920  Fed. Rep. of Germany .............. 3/6

Primary Examiner—Richard J. Apley
Assistant Examiner—David J. Isabella
Attorney, Agent, or Firm—Thomas S. Keaty

[57] ABSTRACT

The present invention provides a biomechanical ankle prosthesis device comprising a main base plate member adapted for connection to an artificial foot; a connector hinge member having an extended portion pivotally connected to one end of the main base plate member so as to pivot relative thereto about the longitudinal axis of the main base plate member, the connector hinge member being further defined as comprising a hinged portion having a longitudinal axis transverse to that of the main base plate member; a leg attachment member having a top portion adapted for connection to a user and its bottom portion being provided with a hinge portion operably connected to the connector hinge member to allow the leg attachment member and the main base plate member to move relative to each other in essentially the same plane about the longitudinal axis of the hinge assembly defined between the connector hinge member and the leg attachment member; and a spring interposed between the leg attachment member and the main base plate member.

3 Claims, 4 Drawing Figures

BIOMECHANICAL ANKLE DEVICE

BACKGROUND OF THE INVENTION

The instant invention relates generally to an artificial prosthestic foot, and more particularly, to a biomechanical ankle type prothesis.

The biomechanics of the foot and ankle represent a complex set of various forces and motions. Those members cannot be each considered as a separate entity, but rather as an integral part of the biomechanics of the entire lower limb. The human body requires a flexible foot in order to adapt to its external environment, which may be flat, uneven, or sloping. Without this freedom of motion a person would be restricted in every day activity.

One basic type of motion sequence that occurs in the ankle joint is dorsiflexion followed by plantar flexion, or vice versa. This sequence about the angle axis of motions is basically perpendicular to the line of forward progression. The ankle joint undergoes plantar flexion which is defined as downward flexion, at the time of initial floor contact (heel strike), which continues until the onset of midstance phase or throughout the first 15% of the walking cycle, and then progressive dorsiflexion which is defined as opposite or upward flexion, occurs from the time of heel-off until the 40% point of the cycle, when again, plantar flexion begins. Thus, during the swing phase, dorsiflexion of the ankle joint takes place until the time of heel strike, when plantar flexion again begins.

Another basic type of motion sequence which occurs in the ankle/foot structure is inversion and eversion. This motion takes place about the subtalar axis, which extends essentially parallel to the longitudinal axis of the foot or perpendicular to the ankle axis. Eversion in simple is moving the sole of the foot outward at the ankle joint. Inversion is moving the sole of the foot inward at the ankle joint. The axis of rotations for these motions is essentially parallel to the line of progression. These maneuvers of the ankle/foot complex allows a person to walk on unlevel surfaces and sloping surfaces without difficulty.

In executing the above motions, the muscles within the lower limb play a vital role in the walking function. By virtue of muscles, controlled and selective movement in the skeletal system is made possible. Muscle movement is actually muscle contraction. Muscle contracture is defined as a condition in which a muscle shortens its length. Therefore, with muscle action on both sides of an axis of a skeletal member, a constant and reccurring control of motion is made possible.

In today's prosthetic field there are various alternatives, many of which are poor designs, to produce the complex actions of the foot/ankle. One such prosthetic device is known as the solid ankle cushion heel foot. That type of prosthetic assembly does not allow a patient to have controlled motion of the foot because it is fabricated of solid material. The motion is predetermined and prefabricated at the factory. Another type of prosthetic device is that known as a single axis foot. That design has only a single axis and can only be ued in above knee amputations because of its size. Also, the subtalar joint action is lacking in both of those prosthetic devices. Among the distinct advantages and features of the present biomechanical ankle is that it not only offers controlled subtalar motion, both plantar and dorsiflexion, but additionally is small enough to be used in a below the knee amputation.

The present biomechanical ankle allows duplication of all types of normal ankle/foot motions, which is, both dorsal and plantar flexion, as well as inversion and eversion. To duplicate the dorsal and plantar flexion of the ankle mortice, controlled acentric and concentric contractures of the ankle/foot must be produced. In the normal ankle mortice these motions occur in a transverse axis and are made possible by a series of related muscles and ligaments. Thus, in prosthetic ankles, the objective is to produce this same action without the use of voluntary muscles. The present biomechanical ankle has the same transverse or ankle axis of the normal ankle mortice. To duplicate the muscle movement of the ankle/foot, which occurs in concention and exertion action, the present device incorporates a control spring which functions in the manner described hereinafter.

As brought out above, the inversion and eversion motions of the normal ankle mortice occur at the subtalar joint, which is the ankle bone structure about the subtalar axis which as mentioned above extends essentially parallel lengthwise to the foot. The subtalar actions of the present biomechanical ankle are realized by virtue of the above referred to spring in combination with the various positioned hinges embodied in its design as described in detail hereinafter.

The primary objective of the instant invention is to provide an artificial prosthesis which meets all the criteria of a prosthetic ankle. Such criteria includes durability; light weight; the capability to support tremendous weight and torque forces, as well as compress to move dynamically similar to a normal foot; and small enough for cosmetic purposes. The most important net objective realized by way of this invention is that a patient can develop a normal gait with the least amount of energy expenditure.

DESCRIPTION OF THE DRAWINGS

The above objects, together with other features and advantages of the instant invention will be apparent to one skilled in the art in light of the details of construction and operation of the present biomechanical ankle prosthesis as shown in the drawings and described in the ensuing detailed disclosure of its preferred embodiment(s) which is particularly pointed out in the appended claims. In the drawings illustrating the preferred embodiment of the present invention, synonymous reference numerals are employed throughout in the various views to refer to identical components.

DESCRIPTION OF THE PREFERRED EMBODIMENT(S)

Figure 1:
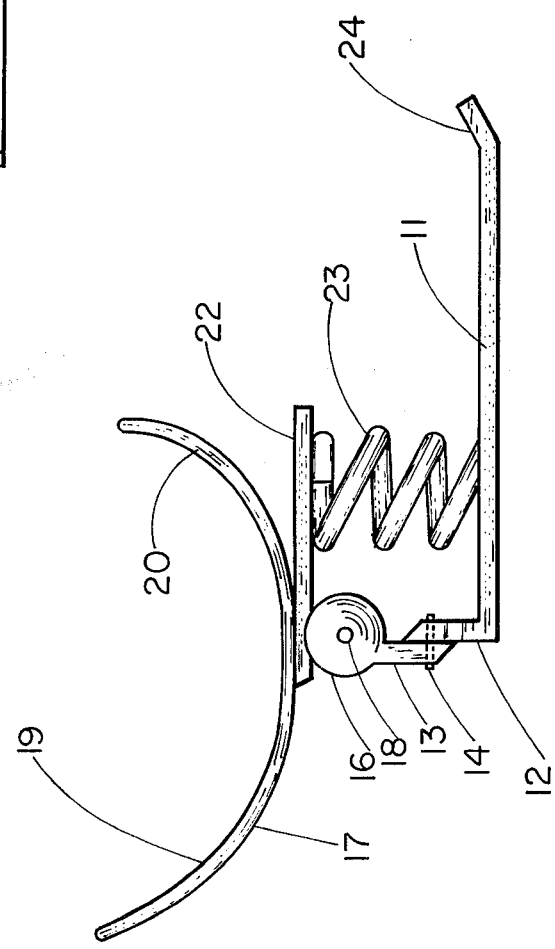
FIG. 1 in the drawings depicts a side elevational view of the present biomechanical ankle prothesis as shown in its normal upright walking position.

Referring to FIG. 1 of the drawings, the present biomechanical ankle device 10 comprises the shoe or base plate member 11 which is adapted to be rigidly affixed to a foot prosthesis in the manner described below. The foot member 11 is provided on one of its ends with the "L" shaped or vertically upward extending portion 12 which is pivotable in relation to the connector hinge member or means 13, both portions 12 and 13 have coaxial bores to receive the longitudinal pin member 14 (shown in phantom line in FIG. 1). The opposite end of the foot support member 11 is provided with the up raised extended portion 24 which functions as a toe brake. The function of the toe brake portion 24 is to provide a base from which the user derives a flowing arc motion when he initiates dorsal flexion or plantar flexion as his foot maneuvers or rotates for lift off during a walking cycle. The exact size and angular position of the toe brake portion 24, and for that matter, of the other components of the present biomechanical ankle prosthesis, will vary according to the size and weight of the user.

Figure 2:
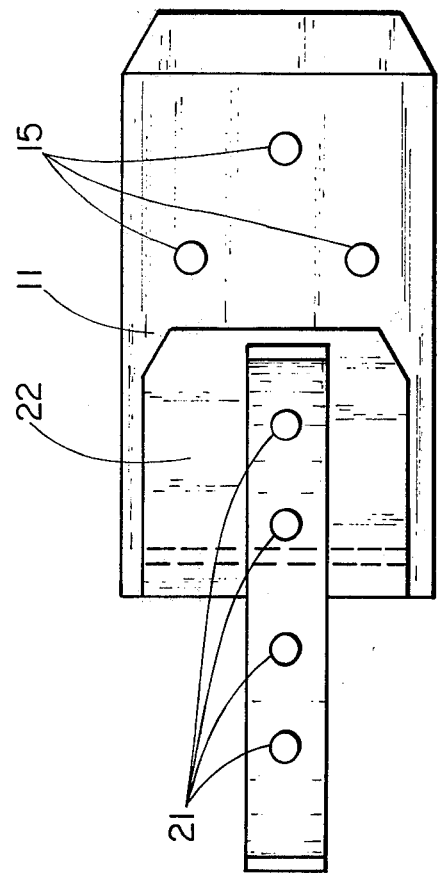
FIG. 2 in the drawings depicts a plan view of the present invention from its position as shown in FIG. 1 of the drawings.

As shown in FIG. 2 of the drawings, the foot plate member 11 is provided with a suitable number of the boreholes 15 for attachment to a prosthetic foot member (not shown) by virtue of conventional screws.

Figure 4:
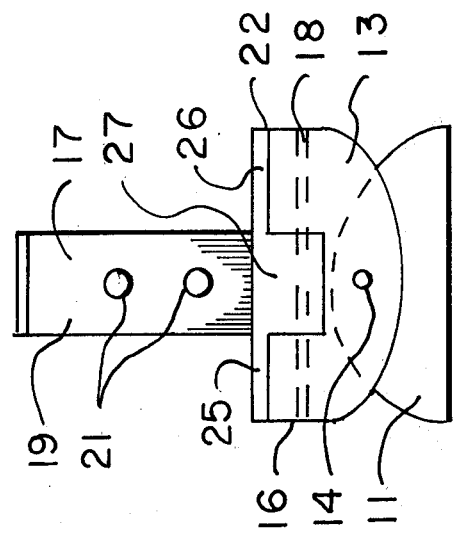
FIG. 4 in the drawings represents a rear elevational or left hand side view of the present prothesis from its position as shown in FIG. 1.

The connector hinge yoke member 13, referring to both FIGS. 1 and 4 of the drawings, is a somewhat "U" shaped member having the journalled extended portions 25 and 26, being bored to receive the traversal pin member or means 18. The member 13 is also bored along its bottom portion to receive the longitudinal pin member or means 14.

The connector hinge yoke member 13 in combination with the foot base member 11 provides for inversion and eversion about the axis of the longitudinal pin means 14. In essence, the axis of the pin means 14 defines the subtalar axis and the transversal axis of the pin means 18 defines the ankle axis of the present biomechanical ankle prosthesis.

Figure 3:
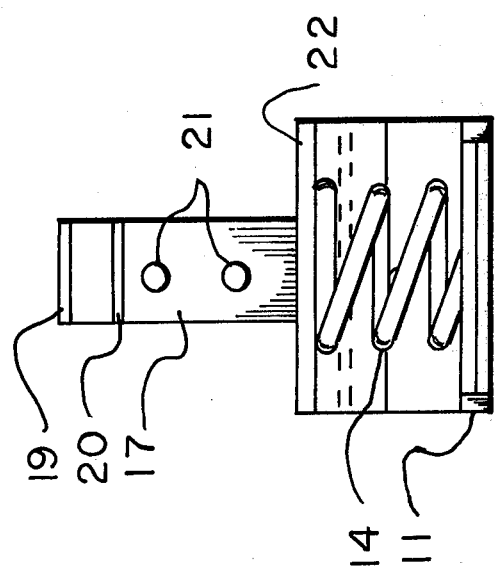
FIG. 3 in the drawings depicts a front elevational or right hand side view of the present prothesis from its position as shown in FIG. 1.

The connector hinge member 13 is pivotally connected to the leg attachment member 17 by virtue of the transversal pin means 18. The member 17 is further defined as preferably comprising the curved upward extending portions 19 and 20 which as further illustrated in FIG. 2 of the drawings are provided with a suitable number of the boreholes 21 to allow rigid attachment to an artificial leg prosthesis (not shown) by conventional screws in the manner well known in the business. Referring also to FIGS. 3 and 4 of the drawings, the leg attachment member assembly 17 is further defined as comprising the spring base connector member 22. The latter is further defined as comprising the downward extending journalled portion 27 which in combination with the journalled portion 16 which further comprises the separate portions 25 and 26 of the connector hinge yoke member 13, forms in essence a clevis joint, the functions of which serves as the ankle axis of the present biomechanical ankle prosthesis.

Referring to both FIGS. 1 and 3 of the drawings, the leg attachment member 17 and the spring base connector member or means 22 are further operably connected to the base plate member 11 by virtue of the interposed spring means 23. The spring means 23 is a high tensile strength spring rigidly affixed to those means whereby it is subjected to both compressive as well as extension forces. The mechanical properties of the spring means 23 are selected according to the size and weight of the user.

By virtue of the above described details of the present invention, its mode of operation is apparent. The leg attachment member 17 is rigidly affixed to an artificial leg prosthesis and the foot member 11 to an artificial foot in the manner well known in the art. The combined assembly is then utilized in the conventional manner and by virtue of the present unique design, the user is able to develop a normal gait during the course of walking.

As known, an initial floor contact during a normal walking cycle requires that there be 12% plantar flexion in an ankle joint and a rapid adversion (for about 10°) in subtalar joint. Therefore, base plate 11 will move downwardly in relation to a vertical axis of the foot and at the same time upwardly in relation to a horizontal axis of the foot.

Then, during a normal walking cycle a progressive-dorsal-plantar flexion occurs with a simultaneous inversion and eversion actions and proceeds well over 50% of a normal walking cycle.

In relation to the device of the present application, it means that the aft portion of base plate 11 is lifted and at the same time moved inwardly.

A lift off which occurs at about 65% of a walking cycle is characterized by maximum plantar flexion (up to 25°) and final inversion-eversion. At this time, the front portion of base plate 11 is lowered down and reaches its substantially most inward position.

The rest of the walking cycle is characterized by a progressive dorsal-plantar flexion, inversion and eversion. At this time, the front portion of base plate 11 is lifted and moved outwardly, so that a new walking cycle can be started after the next initial floor contact.

All these movements are made possible by a substantial flexibility of ankle joint of the present application. It should be noted that a vertical movement of base plate member 11 is restricted by limited rotation of journalled portion 16 about a hinged member 27, this rotation being dependent on the extend of compression of supreme coil 23. A horizontal movement of plate member 11 in relation to connector hinge 13 about the horizontal axis of pin 14 is also restricted by the mechanical characteristics of coil, substantially limiting its horizontal movement.

It will be apparent to one skilled in the art that various changes and modifications can be made in the above described design of the present biomechanical ankle prosthesis without departing from the true scope and spirit of the present invention. For example, the particular shape and configuration of its various components can be changed as long as the basic types of motion are still present. Moreover, the particular configuration of the hinged portions of its members can be changed as long as the members are allowed to hinge relative to each other in the described manner.

In light of the above, it is thus apparent to one skilled in the art that many modifications can be made in the instant invention and what I intend to encompass within the ambit of my invention is that as set forth and particularly pointed out in the appended claims.

What I claim as invention is:

1. Biomechanical ankle prosthesis means comprising:
   (a) a substantially flat main base plate means adapted for connection to an artifical foot; having a perpendicularly extending portion integrally connected to one end of said main base plate means, said perpendicularly extending portion being bored to receive a pin means disposed in a parallel relationship to a longitudinal axis of said main base plate means;
   (b) a vertically extended connector hinge means having its lower portion pivotally connected to said perpendicularly extending portion of said main base plate means through said pin means so as to pivot relative thereto about the longitudinal axis of said main base plate means, thus imitating a rotation in subtalar joint of an ankle, said connector hinge means being further defined as comprising a hinged portion having a longitudinal axis transverse to that of said main base plate means;

(c) leg attachment assembly having an upper portion adapted for connection to an artificial leg means and rigidly attached lower portion comprising a spring base connector member being provided with a hinged portion connected to an upper portion of said connector hinge means to form a clevis joint and to allow said leg attachment assembly to move in a vertical plane relative to said main base plate means, so as to imitate rotation at an ankle axis; and (d) spring coil means interposed between said leg attachment assembly and said main base plate means.

2. The biomechanical ankle prosthesis of 1, further characterized in that said leg attachment assembly is further defined as comprising a curve upper portion and a said hinged porton of said lower portion being integrally connected to said spring base connector member at the rear end thereof and extending downwardly and transversely relative thereto in a position essentially at the center of the curved upper portion, the front end of said spring base connector means extending toward the front and parallel to said main base plate means.

3. The biomechanicl ankle prosthesis means of claim 1 further characterized in that said spring coil means is further defined as comprising a helical coil spring interposed and affixed between the bottom front end of the lower portion of said leg attachment assembly and the top essentially mid portion of said main base plate means.

* * * * *